United States Patent [19]

Ackerman et al.

[11] Patent Number: 5,204,329

[45] Date of Patent: Apr. 20, 1993

[54] TREATMENT OF ORGAN TRANSPLANTATION REJECTION

[75] Inventors: Neil R. Ackerman, Greenville; Bruce D. Jaffee, Wilmington, both of Del.

[73] Assignee: Du Pont Merck Pharmaceutical Company, Wilmington, Del.

[21] Appl. No.: 535,672

[22] Filed: Jun. 11, 1990

[51] Int. Cl.$^5$ .................... A61K 31/47; A61K 37/00

[52] U.S. Cl. .................... 514/15; 514/311; 514/312

[58] Field of Search .................... 514/311, 312, 15

[56] References Cited

U.S. PATENT DOCUMENTS

| | | | |
|---|---|---|---|
| 3,574,840 | 4/1971 | Riviere et al. | 514/311 |
| 3,973,022 | 8/1976 | Goschke | 514/311 |
| 4,117,135 | 9/1978 | Schröder et al. | 514/311 |
| 4,407,803 | 10/1983 | Haviv et al. | 424/258 |
| 4,661,499 | 4/1987 | Young et al. | 514/311 |
| 4,680,299 | 7/1987 | Hesson | 514/311 |
| 4,847,381 | 7/1989 | Sutherland et al. | 546/156 |
| 4,851,409 | 7/1989 | Young et al. | 514/228.2 |
| 4,861,783 | 7/1989 | Ackerman et al. | 514/311 |
| 4,929,626 | 5/1990 | Mohrs et al. | 514/311 |
| 4,968,701 | 11/1990 | Ackerman et al. | 514/312 |

FOREIGN PATENT DOCUMENTS

| | | | |
|---|---|---|---|
| 0190722 | 8/1986 | European Pat. Off. | 215/14 |
| 0231151 | 8/1987 | European Pat. Off. | |
| 1334705 | 6/1970 | United Kingdom | 33/00 |

OTHER PUBLICATIONS

*Chemical Abstracts*, 111 (3): 17327v. Gerdin et al. 1989. Rat Cardiac Allografts Protected with Cyclosporin A are Rejected in the Presence of LS-2616 (Linomide).

*Primary Examiner*—S. J. Friedman
*Attorney, Agent, or Firm*—Blair Q. Ferguson; Margaret A. Horn

[57] ABSTRACT

4-Quinoline-carboxylic acid derivatives, such as 2-(2'-fluoro-1,1'-biphenyl-4-yl)-6-fluoro-3-methyl-4-quinoline carboxylic acid, in combination with other immunosuppressive agents are useful for the treatment and/or prevention of transplantation rejection, graft vs. host disease, autoimmune diseases, and chronic inflammatory disease.

31 Claims, No Drawings

TREATMENT OF ORGAN TRANSPLANTATION REJECTION

BACKGROUND OF THE INVENTION

U.S. Pat. No. 4,680,299 (Hesson), granted Jul. 14, 1987, describes 4-quinoline-carboxylic acid derivatives as tumor inhibiting agents. Commonly assigned European Patent Application Serial No. 89107099.7, published Nov. 2, 1989 described 4-quinoline-carboxylic acid derivatives as immunomodulatory and anti-inflammatory agents.

U.S. Pat. No. 4,847,381 (Sutherland et. al.,) teaches substituted 4-quinoline-carboxylic acid compounds useful for the treatment of arthritis and useful as immunosuppressive agents.

Presently, cyclosporin A, an immunosuppressive agent, used in combination with other adjunctive therapies, such as azathioprine (AZA and corticosteroids, is the treatment of choice for the prevention of organ transplantation rejection. Other immunosuppressive agents, including but not limited to azathioprine, corticosteroids (such as prednisone), OKT3, FK506, mycophenolic acid or the morpholinethylester thereof, 15-deoxyspergualin, rapamycin, mizoribine, misoprostol and anti-interluekin-2 (IL-2) receptor antibodies have been used or are suggested to be useful in the treatment and/or prevention of organ transplantation rejection.

Use of any of these known immunosuppressive compounds, either along or in combination, is associated with a high incidence of side effects such as nephrotoxicity and/or hepatoxicity. The 4-quinoline-carboxylic acid compounds useful in the present invention have a unique mechanism of action compared to other known immunosuppressive agents, and therefore have not been associated with the nephrotoxicity and hepatoxicity seen with other immunosuppressive agents such as cyclosporin A and AZA. In addition, the combination of a 4-quinoline-carboxylic acid with known immunosuppressive agents has a synergistic effect in terms of inhibition of inflammation in animal models. This synergistic effect is seen at suboptimal doses of each immunosuppressive agent, thus, suggesting that known immunosuppressive agents could be used in combination with a 4-quinoline-carboxylic acid compound, each at lower doses with an associated lower incidence of side effects.

SUMMARY OF THE INVENTION

According to the present invention, there are provided methods of treating and/or preventing organ transplantation rejection, graft versus host disease, psoriasis and autoimmune diseases, including but not limited to rheumatoid arthritis, systemic lupus erythematous, multiple sclerosis, myasthenia gravis as well as chronic inflammatory disease including but not limited to Crohn's disease and primary billiary cirrhosis, in a mammal, said methods comprising administering to the mammal in an effective amount for the treatment of a desired aforesaid disease a combination of: (a) at least one immunosuppressive agent preferably selected from the group consisting of cyclosporin A, azathioprine, a corticosteroid such as prednisone or prednisolone, OKT3, FK506, mycophenolic acid or the morpholinethylester thereof, 15-deoxyspergualin, rapamycin, mizoribine, misoprostol and anti-interleukin-2 (IL-2) receptor antibodies, and (b) a compound of the formula:

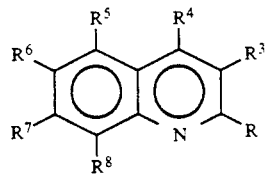

or a pharmaceutically acceptable salt thereof wherein:
R is

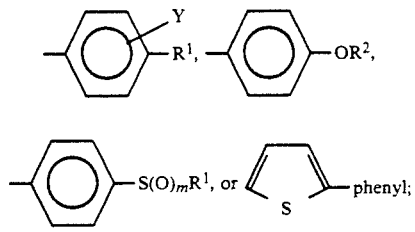

$R^1$ is $CH_3CH_2(CH_3)CH$, alkyl of 5 to 12 carbon atoms, cyclohexyl,

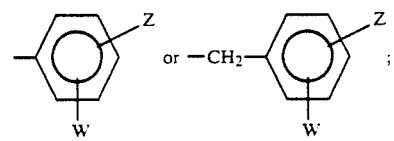

when R is 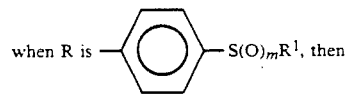, then $R^1$ can be in addition alkyl of 3 to 4 carbon atoms; $R^2$ is

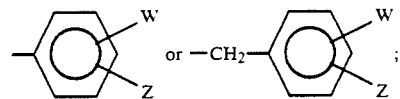

$R^3$ is H, alkoxy of 1 to 3 carbon atoms, alkyl of 1 to 2 carbon atoms, hydroxy or alkanoyloxy of 2 to 6 carbon atoms;

when $R^3$ is hydroxy or alkanoyloxy of 2 to 6 Carbon atoms, $R^1$ can be in addition, trifluoromethyl, halogen, hydroxy, alkyl of 1 to 6 carbon atoms and cycloalkyl of 1 to 6 carbon atoms;

$R^4$ is $CO_2H$ or $CO_2R^{11}$;

$R^5$, $R^6$, $R^7$ and $R^8$ are independently H, F, Cl, Br, I, $CH_3$, $CF_3$, $SCH_3$ or alkyl of 1 to 3 carbon atoms, at least two of $R^5$, $R^6$, $R^7$ and $R^8$ being H;

$R^9$ and $R^{9A}$ are independently H or alkyl of 1 to 3 carbon atoms;

$R^{11}$ is $(CH_2)_{2-4}NR^9R^{9A}$;

W, Y and Z are independently H, F, Cl, Br, alkyl of 1 to carbon atoms, $NO_2$, OH, $CF_3$ or $OCH_3$; and m is 0 or 1;

with the following provisos:
(1) $R^5$, $R^6$ and $R^7$ cannot all be H;
(2) when $R^4$ is $CO_2CH_2CH_2N(CH_3)_2$, $R^6$ is $CH_2CH_3$, or $R^7$ is Cl, $R^1$ cannot be cyclohexyl;

(3) when $R^1$ is cyclohexyl and $R^3$ is H, $R^6$ must be Cl or F, but $R^6$ and $R^8$ cannot both be Cl; and (4) when $R^6$ is CH$_3$, then $R^7$ cannot be Cl.

Current recommended therapy for the prevention of organ transplantation rejection and related disorders, including graft versus host disease, traditionally involves patient treatment with cyclosporin A and adjunctive therapy with corticosteroids and other immunosuppressive drugs (*Immune Modulation Agents and Their Mechanisms*, ISBN 0-8247-7178-8, 1984, pp 191-228, Jacobs and Elgin "Cyclosporin A, Current Status, Including the Cape Town Experience" *Transplantation and Clinical Immunology*, Volume XX Combined Immunosuppressive suppressive Therapy in Transplantation ISBN 444-81068-4, 1989). Our results indicate that 2-phenyl-4-quinoline-carboxylic acids and their derivatives will be useful as agents to be used in combination with compounds currently used in these clinical regimens.

The significant clinically observed toxicities associated with cyclosporin A (nephrotoxicity) and AZA (hepatoxicity), have not been seen with 2-phenyl-4-quinoline-carboxylic acids and their derivatives. Moreover, 2-phenyl-4-quinoline-carboxylic acids and their derivatives have a unique mechanism of action (inhibition of dihydroorotate dehydrogenase) which is distinct from other available immunosuppressive agents. Our results show that 2-phenyl-4-quinoline-carboxylic acids and their derivatives have synergistic activity when included in the currently accepted regimen of drug therapy for the prevention of organ transplantation rejection and related complications. More particularly, these 2-phenyl-4-quinoline-carboxylic acid derivatives should be useful at reduced doses of both the quinoline-carboxylic acid compound and other immunosuppressive agents used in combination therewith.

PREFERRED EMBODIMENTS

Preferred compounds useful in the present invention have the formula:

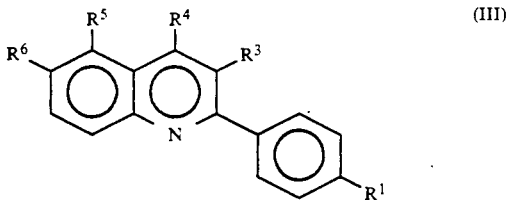

or a pharmaceutically acceptable salt thereof wherein:

$R^1$ is cyclohexyl; phenyl; phenyl substituted with one halogen; alkyl of 1 to 5 carbon atoms or CF$_3$; phenoxy; or phenoxy substituted with one halogen or alkyl of 1 to 5 carbon atoms; and/or $R^3$ is H or alkyl of 1 to 2 carbon atoms; and/or $R^4$ is CO$_2$H, a sodium or potassium salt thereof; or CO$^2$R$^{11}$; and/or $R^5$ and $R^6$ are independently H, halogen, CH$_3$ or CF$_3$; and/or $R^7$ and $R^8$ are independently H or halogen; and/or $R^{11}$ is (CH$_2$)$_{2-4}$NR$^9$R$^{9A}$; and/or $R^9$ and $R^{9A}$ are independently alkyl of 1 to 3 carbon atoms;

provided that $R^5$, $R^6$ and $R^7$ cannot all be H; when $R^1$ is cyclohexyl and $R^3$ is H, $R^6$ must be Cl or F, but $R^6$ and $R^8$ cannot both be Cl; when $R^6$ is CH$_3$, then $R^7$ cannot be Cl; and when $R^4$ is CO$_2$H, $R^1$ or $R^2$ is phenyl, and $R^5$, $R^7$ and $R^8$ are H, then $R^6$ cannot be Br.

More preferred compounds useful in this invention have the formula:

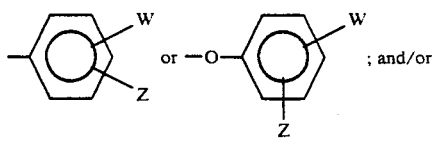

wherein $R^1$ is cyclohexyl,

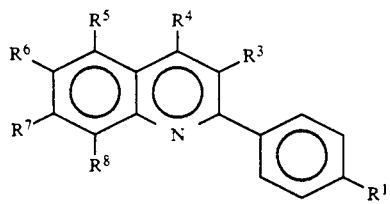

$R^3$ is H or alkyl of 1 to 2 carbon atoms; and/or $R^4$ is CO$_2$H, a sodium or potassium salt thereof, or CO$_2$R$^{11}$; and/or $R^5$ and $R^6$ are independently H, halogen or CF$_3$ provided that both $R^5$ and $R^6$ are not hydrogen; and/or $R^{11}$ is (CH$_2$)$_{2-4}$NR$^9$R$^{9A}$; and/or $R^9$ and $R^{9A}$ are independently alkyl of 1 to 3 carbon atoms, and/or W and Z are independently H, halogen, alkyl of 1 to 5 carbon atoms or CF$_3$;

provided that when $R^1$ is phenyl or phenoxy, and $R^5$ is H, then $R^6$ cannot be Br; and that when $R^1$ is cyclohexyl and $R^3$ is H, $R^6$ must be Cl or F.

Specifically preferred compounds useful in this invention are:

(1) 2-(1,1'-biphenyl-4-yl)-5-chloro-3-methyl-4-quinoline carboxylic acid, sodium or potassium salt (2) 2-(1,1'-biphenyl-4-yl)-6-fluoro-3-methyl-4-quinoline carboxylic acid, sodium or potassium salt (3) 6-fluoro-3-methyl-2-(4-phenoxyphenyl)-4-quinoline carboxylic acid, sodium or potassium salt (4) 2-(4'-bromo-1,1'-biphenyl-4-yl)-6-fluoro-3-methyl-4-quinoline carboxylic acid, sodium or potassium salt (5) 2-(2'-fluoro-1,1'-biphenyl-4-yl)-6-fluoro-3-methyl-4-quinoline carboxylic acid, sodium or potassium salt.

DETAILED DESCRIPTION OF THE INVENTION

The 4-quinoline-carboxylic acid derivatives useful in this invention are described in and prepared by methods set forth in U.S. Pat. Nos. 4,680,299 and 4,847,381, the disclosure, synthesis, and synthesis examples of which are hereby incorporated by reference. The isolation of the FK506 natural product is described in European Patent Application publication number 240,773, published 10/14/87 and the chemical synthesis of FK506 is described in Jones et al. (1989) *J. Am. Chem. Soc.* 11:1157-1159.

The preparation of azathioprine is described in U.S. Pat. No. 3,056,785 issued to Burroughs Wellcome. LOC Azathioprine is available as Imuran®, for which the product information, including dosage and administration, is given in *Physician' Desk Reference* 44th Edition, 1990, pp 777-778.

The preparation of cyclosporin A is described in U.S. Pat. No. 4,117,118 issued to Sandoz. Cyclosporin A is available as Sandimmune ®, for which the product information, including dosage and information, is given in *Physician' Desk Reference* 44th Edition, 1990, pp 1950–1952.

The preparation of prednisone is described in U.S. Pat. Nos. 2,897,216 and 3,134,718 issued to Schering. Prednisone is available commercially from several manufacturers as are other corticosteroids (see generally, *Physicians' Desk Reference, supra*).

Murine monoclonal antibody to the human T3 antigen (herein referred to as OKT3) is available as Orthoclone OKT ®3, for which the product information, including dosage and administration and references to methods of preparation, is given in PDR, 1990, pp 1553–1554.

The preparation of mycophenolic acid is described in British patents 1,157,099; 1,157,100; and 1,158,387 issued to ICI.

15-dioxyspergualin is a derivative of spergualin discovered in culture filtrates of the bacterial strain BGM162-aFZ as reported in Ochiai, T., Hori, S., Nakajimak, et. al. Prolongation of Rat Heart Allograft Survival by 15-desoxyspergualin, J. Antibiot (Tokyo) 1987; 40:249.

Mizoribine is described in U.S. Pat. No. 3,888,843 issued to Toyo Jozo.

Misoprostol, a prostaglandin (PGE1) analog, is described in U.S. Pat. No. 3,965,143 assigned to Searle and U.S. Pat. No. 4,132,738 assigned to Miles. Rapamycin is described in U.S. Pat. Nos. 4,650,803; 4,316,885; 4,885,171; 3,993,749 and U.S. Pat. No. 3,929,992, all assigned to Ayerst.

Antibodies to the IL-2 receptor protein are described in U.S. Pat. Nos. 4,578,335 and 4,845,198 (Immunex) and U.S. Pat. No. 7/341,361 and U.S. Pat. No. 4,892,827 issued to Pastan et. al.

Utility

Contact Sensitivity Response to DNFB in Mice

Balb/c female mice ($\simeq$20 g, Charles River) were sensitized on the shaved abdomen with 25 $\mu$l of 0.5% 2,4-dinitrofluorobenzene (DNFB, Eastman Kodak Co.) in a vehicle of 4:1 acetone:olive oil on days 0 and 1. Mice were ear challenged with 20 $\mu$l of 0.2% DNFB in a vehicle of 4:1 acetone:olive oil on day 5. An identical segment of the ear was measured immediately before challenge and 24 hours later with an engineer's micrometer. Ear swelling was expressed as the difference in ear thickness before and after challenge in units of $10^{-4}$ inches $\pm$ SEM. Percent suppression was calculated as:

$$\% \text{ Suppression} = 1 - \frac{\text{compound treated} - \text{negative control}}{\text{positive control} - \text{negative control}} \times 100$$

Compounds were administered orally from day 0 through day 6 and were prepared in 0.25% Methocel ® (Dow Chemical Co.). Control animals received only vehicle (0.25% Methocel ®). Negative controls were not sensitized on days 0 and 1 but were ear challenged on day 5. Ten mice were used per group. Results with compounds of invention are shown in Tables 1–4.

Results of the biological tests described below establish that the combination of (1) a 4-quinoline-carboxylic acid derivative and (2) at least one additional immunosuppressive agent, such as cyclosporin A, azathioprine or prednisone, has the effect of suppressing or inhibiting the contact sensitivity response to 2,4-dinitrofluorobenzene (DNFB) in mice.

Contact sensitivity to DNFB is a form of delayed-type hypersensitivity which has been extensively studied to gain an understanding of the regulation of immunologic processes (Claman et. al. (1980), *Immunological Rev.* 50:105–132). This reaction is mediated by T lymphocytes that become sensitized to antigen by proliferating and developing into mature effector cells (Claman et. al. (1980), *Immunological Rev.* 105–132). This cell-mediated immune response (T-cell mediated immunity) is central to many disease states such as organ transplantation rejection and graft versus host disease (Benaceraf and Unanue (1979), *Textbook of Immunology*, Williams & Wilkins Co.,; Eisen (1980), *Immunology, An Introduction to Molecular and Cellular Principles of the Immune Responses*, Harper & Row, Inc.; Loveland and McKenzie (1982), *Inflammation, Basic Principles and Clinical Correlates*, Raven Press).

A representative 4-quinoline-carboxylic acid derivative, 2-(2'-fluoro-1,1'-biphenyl-4-yl)-6-fluoro-3-methyl-4-quinoline carboxylic acid (Example 28, U.S. Pat. No. 4,680,299; hereinafter referred to as Example 28), was tested individually (Table 1) as was cyclosporin A (Table 1) and in combination with cyclosporin A in the DNFB contact sensitivity model (Table 2).

TABLE 1

| Treatment | Dose (mg/kg) | Ear[a] Swelling (units $\pm$ SEM) | % Suppression | ED$_{50}$ mg/kg |
|---|---|---|---|---|
| Negative | Vehicle | 0.74 $\pm$ 0.52 | — | — |
| Positive | Vehicle | 74.11 $\pm$ 3.78 | 0 | — |
| Cyclosporin A | 2.0 | 56.15 $\pm$ 3.74 | 24.48 | 70.00 |
|  | 10.0 | 66.58 $\pm$ 3.75 | 10.27 |  |
|  | 50.0 | 47.90 $\pm$ 3.76 | 35.72 |  |
|  | 100.0 | 7.80 $\pm$ 2.04 | 90.37 |  |
| Example 28 | 0.4 | 51.95 $\pm$ 2.33 | 30.20 | 0.95 |
|  | 2.0 | 25.61 $\pm$ 3.39 | 66.10 |  |
|  | 10.0 | 6.40 $\pm$ 1.09 | 92.28 |  |
|  | 20.0 | 4.75 $\pm$ 1.20 | 94.53 |  |

[a]Increase in ear thickness from day 5 to day 6, unit = $10^{-4}$ inches

TABLE 2

Immunosuppressive Effect (% Suppression of Ear Swelling) of the Combination of Example 28 and Cyclosporin A in a Mouse DFNB Contact Sensitivity Model

| | Cyclosporin A (mg/kg) | | | | | | | | Cyclosporin A ED$_{50}$ (mg/kg) |
|---|---|---|---|---|---|---|---|---|---|
| | 0 | 6.3 | 12.5 | 25.0 | 30.0 | 50.0 | 70.0 | 100.0 | |
| Ex. 28 | | | | | | | | | |

TABLE 2-continued

Immunosuppressive Effect (% Suppression of Ear Swelling) of the Combination of Example 28 and Cyclosporin A in a Mouse DFNB Contact Sensitivity Model

| | Cyclosporin A (mg/kg) | | | | | | | | Cyclosporin A ED$_{50}$ (mg/kg) |
|---|---|---|---|---|---|---|---|---|---|
| | 0 | 6.3 | 12.5 | 25.0 | 30.0 | 50.0 | 70.0 | 100.0 | |
| (mg/kg) | | | | | | | | | |
| 0 | 0 | −9.9 ± 7.2 | −4.0 ± 2.6 | 0.1 ± 3.5 | 4.2 ± 4.9 | 33.6 ± 5.7 | 68.9 ± 1.2 | 92.5 ± 2.0 | 60.0 |
| 0.1 | 6.5 ± 2.9 | 7.4 ± 13.2 | 1.5 ± 8.0 | 8.7 ± 9.6 | — | 28.8 ± 11.4 | — | — | >50.0 |
| 0.3 | 7.3 ± 2.4 | 10.2 ± 17.6 | 15.2 ± 7.5 | 3.8 ± 7.1 | −1.7 ± 13.4 | 44.7 ± 7.7 | 66.7 ± 3.6 | — | 52.0 |
| 1.0 | 31.4 ± 3.3 | 51.9 ± 4.6 | 62.1 ± 3.4 | 77.0 ± 8.5 | 84.6 ± 3.3 | 90.8 ± 1.7 | 94.6 ± 4.0 | — | <6.3 |
| 3.0 | 91.9 ± 2.3 | 97.0 ± 1.4 | 99.1 ± 3.8 | 95.7 ± 3.2 | 93.6 ± 4.3 | 93.9 ± 4.5 | 92.0 ± 6.2 | — | <6.3 |
| 10.0 | 93.9 ± 2.4 | — | — | — | 91.5 ± 8.0 | 88.3 ± 9.0 | 86.5 ± 7.1 | — | <6.3 |
| Ex. 28 ED$_{50}$ (mg/kg) | 1.4 | 1.0 | 0.8 | 0.7 | 0.4 | 0.4 | <0.3 | | |

As shown in Table 2, test results with mice receiving the combination treatment of Example 28 and cyclosporin A (CSA) demonstrate that the coadministration of suboptimal doses of each agent (Example 28 at 1.0 mg/kg and CSA at 30.0 mg/kg) produced strong suppression of this T-cell-mediated immune response. These data demonstrate a remarkable synergistic effect of the two compounds using this combination therapy. Whereas Example 28 alone at 1.0 mg/kg results in a 31.4% suppression of this immune response and cyclosporin A alone at 30.0 mg/kg results in only a 4.2% suppression of immune response, when these agents are administered in combination at these suboptimal doses (1.0 mg/kg Ex. 28 and 30 mg/kg CSA), an 84.6% suppression of the immune response was observed. Thus, the immunosuppressive effect of the agents used in combination greatly exceeds the simple addition of the effect of each agent used alone. As shown in Table 2, treatment with Example 28 at a dose of 1.0 mg/kg reduced the effective ED$_{50}$ of cyclosporin A from 60 mg/kg to <6.3 mg/kg.

A similar synergism was observed when Example 28 was administered in combination with azathioprine at suboptimal doses (Table 3). Thus, Example 28 at 1.0 mg/kg and azathioprine at 12.5 mg/kg in combination resulted in a 62.5% immunosuppressive, whereas when used individually these agents at these suboptimal doses only resulted in 31.4% suppression and 15.9% suppression, respectively.

dose basis or on a cumulative basis. For example, the number of days on which dosing occurs may be reduced. This is shown in Table 4, wherein dosing was only at day 0 and 1, whereas in previous examples, dosing was on day 0–6.

TABLE 4

Immunosuppressive Effect (% Suppression of Ear Swelling) of the Combination of Example 28 and Cyclosporin A in a Mouse DNFB Contact Sensitivity Model

| Group[a]/Treatment | mg/kg | ΔEar Swelling[b] | % Suppression |
|---|---|---|---|
| Negative Control[c] | — | 5.8 ± 0.6 | — |
| Positive Control | — | 68.6 ± 3.7 | — |
| Ex. 28 | 20.0 | 59.6 ± 2.5 | 14.4 |
| CSA | 100.0 | 71.8 ± 3.2 | −5.1 |
| Ex. 28 & CSA | 20.0 + 100.0 | 10.8 ± 1.5 | 92.0 |

[a]Group of 10 Balb/c female mice were sensitized on days 0 & 1 (0.5% DNFB).
[b]All mice were ear challenged on day 5 (0.2% DNFB) and measured on day 6.
[c]Nonsensitized control.

The data show that the combination when dosed on days 0 and 1 yielded 92% suppression, whereas cyclosporin A used alone at 100 mg/kg (its optimal dose when administered on days 0–6), when dosed on day 0 and was ineffective (−5.1% suppression).

Current recommended therapy for the prevention of organ transplantation rejection and related disorders, such as graft versus host disease, involves patient treatment with cyclosporin A and adjunctive therapy with corticosteroids and other immunosuppressive drugs.

TABLE 3

Immunosuppressive Effect (% Suppression of Ear Swelling) of the Combination of Example 28 and Azathioprine in a Mouse DFNB Contact Sensitivity Model

| | Azathioprine (mg/kg) | | | | | | Azathioprine ED$_{50}$ (mg/kg) |
|---|---|---|---|---|---|---|---|
| | 0 | 6.3 | 12.5 | 25.0 | 50.0 | 100.0 | |
| Ex. 28 (mg/kg) | | | | | | | |
| 0 | 0 | 2.5 ± 4.2 | 15.9 ± 3.3 | 29.7 ± 4.1 | 72.1 ± 3.1 | 97.7 ± 1.6 | 38.0 |
| 0.1 | 6.5 ± 2.8 | 11.5 ± 10.2 | 20.9 ± 6.1 | 33.6 ± 5.6 | 78.5 ± 3.0 | — | 42.0 |
| 0.3 | 7.3 ± 2.4 | 1.7 ± 7.7 | 25.9 ± 7.5 | 30.0 ± 9.2 | 72.0 ± 3.7 | 101.2 ± 0.5 | 43.0 |
| 1.0 | 31.4 ± 3.3 | 38.4 ± 3.8 | 62.4 ± 3.8 | 71.6 ± 3.8 | 90.3 ± 3.4 | 99.6 ± 3.3 | 7.5 |
| 3.0 | 91.9 ± 2.3 | 94.0 ± 2.8 | 96.3 ± 2.7 | 97.3 ± 1.9 | 99.2 ± 4.3 | 100.5 ± 0.2 | <6.3 |
| 10.0 | 93.9 ± 2.4 | — | — | 100.1 ± 2.2 | 101.4 ± 4.4 | 101.5 ± 3.8 | <6.3 |
| Ex. 28 ED$_{50}$ (mg/kg) | 1.4 | 1.3 | 0.8 | 0.7 | <0.1 | <0.1 | |

As the data in Tables 2 and 3 suggest, a lower dose of each immunosuppressive agent can be used in the combination of the present invention while maintaining an effective level of suppression. The dose of the combination to be administered could be reduced on a single The present results show that 4-quinoline-carboxylic acid derivatives, such as 2-(2'-fluoro-1,1'-biphenyl-4-yl)-6-(fluoro-3-methyl-4-quinoline carboxylic acid, will be useful as drugs to be used in conjunction with current clinical regimens in synergistically effective amounts. The clinically observed toxicities associated with cyclosporin A (nephrotoxicity), and AZA (hepatoxicity), have not been seen with the 4-quinoline-carboxylic acid derivatives useful in this invention. Moreover, the 4-quinoline-carboxylic acids derivatives useful in this invention, such as Example 28, have a unique mechanism of action, i.e., inhibition of dihydroorotate dehydrogenase and consequent inhibition of pyrimidine nucleotide biosynthesis (Chen et. al. (1986) *Cancer Research*, 46:5014–5019). By combining a 4-quinoline-carboxylic acid compound of the present invention with another immunosuppressive agent, lower doses of each agent or less frequent administration of each agent, can be used with comparable effectiveness and lower potential for toxic side effects.

The present results show that Example 28 and related 4-quinoline-carboxylic derivatives should be useful when included in combination with other drugs used in current regimens of drug therapy for the prevention of organ transplantation rejection and related disorders (Jacobs and Elgin (1984) "Cyclosporin A, Current Status, Including the Cape Town Experience", in *Immune Modulation Agents and Their Mechanisms*, pp 191–228, *Transplantation and Clinical Immunology*, Volume XX Combined Immunosuppressive Therapy in Transplantation ISBN 0-444-81068-4, 1989.

DOSAGE FORMS

The immunosuppressive compounds (active ingredients) of this invention, including at least one -quinoline-carboxylic acid compound and at least one immunosuppressive agent preferably selected from the group consisting of, but not limited to: cyclosporin A, azathioprine, corticosteroids such as prednisone, OKT3, FK506, mycophenolic acid or the morpholinethylester thereof, 15-dioxyspergualin, rapamycin, mizoribine, misoprostol and anti-interleukin-2 (IL-2) receptor antibodies, can be administered to treat immunomodulatory disorders and inflammatory diseases and particularly to prevent/treat organ transplantation rejection, graft versus host disease, psoriasis and related disorders, by any means that produces contact of the active ingredient(s) with the agent's site of action in the body of a mammal. The combination therapy can be administered by any conventional means available for use in conjunction with pharmaceuticals; either as individual therapeutically active ingredients or in a combination of therapeutically active ingredients. They can be administered alone, but are generally administered with a pharmaceutical carrier selected on the basis of the chosen route of administration and standard pharmaceutical practice.

The dosage administered will be an immunosuppressive effective amount of active ingredient(s) and will, of course, vary depending upon known factors such as the pharmacodynamic characteristics of the particular active ingredient, and its mode and route of administration; age, health, and weight of the recipient; nature and extent of symptoms; kind of concurrent treatment, frequency of treatment, and the effect desired. Usually a daily dosage of active ingredient can be about 0.1 to 400 milligrams per kilogram of body weight. Ordinarily 1 to 100, and preferably 0.1 to 10 milligrams per kilogram per day is effective to obtain desired results.

Pharmaceutical compositions containing the immunosuppressive agents of this invention alone or in combination, can be made by those skilled in the art, using references such as *Remington's Pharmaceutical Sciences*, A. Osol, a standard reference text in this field. The active ingredients can be administered (alone or in combination) orally in solid dosage forms such as elixirs, syrups, and suspensions, or can also be administered parenterally in sterile liquid dosage forms.

These dosage forms can generally be used when the compounds of this invention are administered stepwise in conjunction with another therapeutic agent. When the drugs are administered in physical combination, the dosage form and administration route should be selected for compatibility with both drugs.

What is claimed is:

1. A method of treating organ transplantation rejection in a mammal comprising administering to the mammal a synergistically effective amount of a combination of (a) at least one immunosuppressive agent, selected from the group consisting of cyclosporin A, azathioprine, FK506, mycophenolic acid or the morpholinethylester thereof, or rapamycin, and (b) at least one compound of the formula:

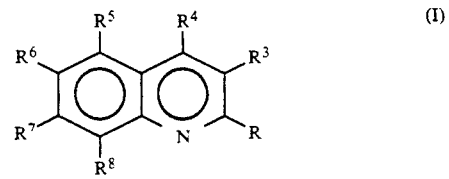

or a pharmaceutically acceptable salt thereof, wherein:
R is

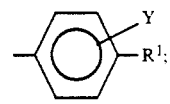

$R^1$ is

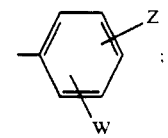

$R^3$ is H, alkoxy of 1 to 3 carbon atoms, alkyl of 1 to 2 carbon atoms, or hydroxy;
$R^4$ is $CO_2H$;
$R^5$, $R^6$, $R^7$ and $R^8$ are independently H, F, Cl, Br, I, $CH_3$, $CF_3$, or alkyl of 1 to 3 carbon atoms, at least two of $R^5$, $R^6$, $R^7$ and $R^8$ being H;
W, Y and Z are independently H, F, Cl, Br, alkyl of 1 to 5 carbon atoms, $NO_2$, OH, $CF_3$ or $OCH_3$;
(1) $R^5$, $R^6$ and $R^7$ cannot all be H; and
(4) when $R^6$ is $CH_3$, then $R^7$ cannot be Cl.

2. A method of treating organ transplantation rejection in a mammal comprising administering to the mammal a synergistically effective amount of a combination of (a) at least one immunosuppressive agent, selected from the group consisting of cyclosporin A, azathioprine, FK506, mycophenolic acid or the morpholinethylester thereof, or rapamycin and (b) at least one compound of the formula:

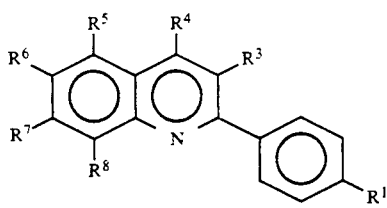

or a pharmaceutically acceptable salt thereof wherein:
$R^1$ is phenyl; phenyl substituted with one halogen;
$R^3$ is H or alkyl of 1 or 2 carbon atoms;
$R^4$ is H or alkyl of 1 or 2 carbon atoms;
$R^4$ is $CO_2H$, a sodium or potassium salt thereof;
$R^5$ and $R^6$ are independently H, halogen, $CH_3$ or $CF_3$;
$R^7$ and $R^8$ are independently H or halogen;
provided that $R^5$, $R^6$ and $R^7$ cannot all be H; and when $R^6$ is $CH_3$, then $R^7$ cannot be Cl.

3. A method of treating organ transplantation rejection in a mammal comprising administering to the mammal a synergistically effective amount of a combination of (a) at least one immunosuppressive agent, selected from the group consisting of cyclosporin A, azathioprine, FK506, mycophenolic acid or the morpholinethylester thereof, or rapamycin, and (b) at least one compound of the formula:

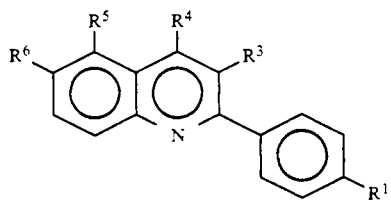

or a pharmaceutically acceptable salt thereof wherein:
$R^1$ is

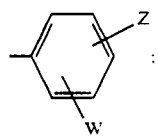

$R^3$ is H or alkyl of 1 or 2 carbon atoms;
$R^4$ is $CO_2H$, a sodium or potassium salt thereof;
$R^5$ and $R^6$ are independently H, halogen or $CF_3$ provided that both $R^5$ and $R^6$ are not hydrogen;
W and Z are independently H, halogen, alkyl of 1 to 5 carbon atoms or $CF_3$.

4. The method of claim 1 wherein the compound of formula (I) is 2-(1,1'-biphenyl-4-yl)-5-chloro-3-methyl-4-quinoline carboxylic acid, or the sodium or potassium salt thereof.

5. The method of claim 1 wherein the compound of formula (I) is 2-(1,1'-biphenyl-4-yl)-6-fluoro-3-methyl-4-quinoline carboxylic acid, or the sodium or potassium salt thereof.

6. The method of claim 1 wherein the compound of formula (I) is 6-fluoro-3-methyl-2-(4-phenoxyphenyl)-4-quinoline carboxylic acid, the sodium or potassium salt.

7. The method of claim 1 wherein the compound of formula (I) is 2-(4'-bromo-1,1'-biphenyl-4-yl)-6-fluoro--methyl-4-quinoline carboxylic acid, sodium or potassium salt.

8. The method of claim 1 wherein the compound of formula (I) is 2-(2'-fluoro-1,1'-biphenyl-4-yl)-6-fluoro-3-methyl-4-quinoline carboxylic acid, sodium or potassium salt.

9. The method of claim 4 wherein the 4-quinolinecarboxylic acid compound is used in combination with cyclosporin A.

10. The method of claim 8 wherein the 4-quinolinecarboxylic acid compound is used in combination with cyclosporin A.

11. The method of claim 4 wherein the 4-quinolinecarboxylic acid compound is used in combination with FK506.

12. The method of claim 8 wherein the 4-quinolinecarboxylic acid compound is used in combination with FK506.

13. The method of claim 4 wherein the 4-quinolinecarboxylic acid compound is used in combination with azathioprine.

14. The method of claim 8 wherein the 4-quinolinecarboxylic acid compound is used in combination with azathioprine.

15. The method of claim 4 wherein the 4-quinolinecarboxylic acid compound is used in combination with mycophenolic acid or the morpholinethylester thereof.

16. A method of claim 8 wherein the 4-quinoline-carboxylic acid compound is used in combination with mycophenolic acid or the morpholinethylester thereof.

17. A method of treating rheumatoid arthritis, systemic lupus erythematous, multiple sclerosis, myasthenia gravis, graft versus host disease, psoriasis, Crohn's disease, or primary biliary cirrhosis in a mammal comprising administering to the mammal a synergistically effective amount for the treatment of a desired aforesaid disease, a combination of (a) at least one immunosuppressive agent, selected from the group consisting of cyclosporin A, azathioprine, FK506, mycophenolic acid or the morphilinethylester thereof, or rapamycin, and (b) at least one compound of the formula:

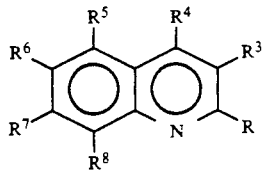

or a pharmaceutically acceptable salt thereof wherein:
R is

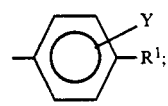

$R^1$ is

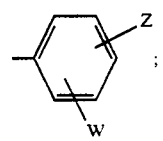

$R^3$ is H, alkoxy of 1 to 3 carbon atoms, alkyl of 1 to 2 carbon atoms, or hydroxy;

$R^4$ is $CO_2H$;

$R^5$, $R^6$, $R^7$ and $R^8$ are independently H, F, Cl, Br, I, $CH_3$, $CF_3$, or alkyl of 1 to 3 carbon atoms, at least two of $R^5$, $R^6$, $R^7$ and $R^8$ being H;

W, Y and Z are independently H, F, Cl, Br, alkyl of 1 to 5 carbon atoms, $NO_2$, OH, $CF_3$ or $OCH_3$;

with the following provisos:

(1) $R^5$, $R^6$ and $R^7$ cannot all be H; and (4) when $R^6$ is $CH_3$, then $R^7$ cannot be Cl.

18. The method of claim 17 wherein the compound of formula (I) is 2-(1,1'-biphenyl-4-yl)-5-fluoro-3-methyl-4-quinoline carboxylic acid, or the sodium or potassium salt thereof.

19. The method of claim 17 wherein the compound of formula (I) is 2-(1,1'-biphenyl-4-yl)-6-fluoro-3-methyl-4-quinoline carboxylic acid, or the sodium or potassium salt thereof.

20. The method of claim 17 wherein the compound of formula (I) is 6-fluoro-3-methyl-2-(4-phenoxyphenyl)-4-quinoline carboxylic acid, or the sodium or potassium salt thereof.

21. The method of claim 17 wherein the compound of formula (I) is 2-(4'-bromo-1,1'-biphenyl-4-yl)-6-fluoro-3-methyl-4-quinoline carboxylic acid, or the sodium or potassium thereof.

22. The method of claim 17 wherein the compound of formula (I) is 2-(2'-fluoro-1,1'-biphenyl-4-yl)-6-fluoro-3-methyl-4-quinoline carboxylic acid, or the sodium or potassium thereof.

23. The method of claim 18 wherein the 4-quinoline-carboxylic acid compound is used in combination with cyclosporin A.

24. The method of claim 22 wherein the 4-quinoline-carboxylic acid compound is used in combination with cyclosporin A.

25. The method of claim 18 wherein the 4-quinoline-carboxylic acid compound is used in combination with FK506.

26. The method of claim 22 wherein the 4-quinoline-carboxylic acid compound is used in combination with FK506.

27. The method of claim 18 wherein the 4-quinoline-carboxylic acid compound is used in combination with azathioprine.

28. The method of claim 22 wherein the 4-quinoline-carboxylic acid compound is used in combination with azathioprine.

29. The method of claim 18 wherein the 4-quinoline-carboxylic acid compound is used in combination with mycophenolic acid or the morpholinethylester thereof.

30. The method of claim 22 wherein the 4-quinoline-carboxylic acid compound is used in combination with mycophenolic acid or the morpholinethylester thereof.

31. A pharmaceutical composition comprising a pharmaceutically acceptable carrier and at least one immunosuppressive agent(other than a 4-quinoline-carboxylic acid derivative) and at least one compound of Formula I, as defined in claim 1, as a combined preparation permitting the simultaneous or separated sequential use of said immunosuppressive agent and said 4-quinoline-carboxylic acid derivative of Formula I.

* * * * *